US012016981B2

(12) United States Patent
Shave et al.

(10) Patent No.: US 12,016,981 B2
(45) Date of Patent: Jun. 25, 2024

(54) FRAGRANCE DIFFUSER

(71) Applicant: The Yankee Candle Company, Inc., South Deerfield, MA (US)

(72) Inventors: Robert Earle Shave, Greenfield, MA (US); Allison Rachel McGlynn, Amherst, MA (US); Herbert Samuel Dodson, China Grove, NC (US)

(73) Assignee: The Yankee Candle Company, Inc., South Deerfield, MA (US)

( * ) Notice: Subject to any disclaimer, the term of this patent is extended or adjusted under 35 U.S.C. 154(b) by 92 days.

(21) Appl. No.: 17/661,205

(22) Filed: Apr. 28, 2022

(65) Prior Publication Data

US 2022/0347335 A1 Nov. 3, 2022

Related U.S. Application Data

(60) Provisional application No. 63/181,432, filed on Apr. 29, 2021.

(51) Int. Cl.
*B05B 17/06* (2006.01)
*A61L 9/12* (2006.01)

(52) U.S. Cl.
CPC .......... *A61L 9/127* (2013.01); *B05B 17/0684* (2013.01); *A61L 2209/132* (2013.01); *A61L 2209/133* (2013.01)

(58) Field of Classification Search
CPC .............. A61L 9/127; A61L 2209/132; A61L 2209/133; A61L 9/14; A61L 2209/10; B05B 17/0684; B05B 17/0607
See application file for complete search history.

(56) References Cited

U.S. PATENT DOCUMENTS

| 11,407,000 | B2* | 8/2022 | Hasik | A01M 1/2077 |
| 2008/0128926 | A1* | 6/2008 | Hsu | F24F 6/02 261/81 |
| 2015/0054182 | A1* | 2/2015 | Kawashima | B05B 15/60 261/78.2 |
| 2018/0161473 | A1* | 6/2018 | Xu | B05B 17/0607 |

* cited by examiner

Primary Examiner — Qingzhang Zhou
(74) Attorney, Agent, or Firm — Husch Blackwell LLP

(57) ABSTRACT

A diffuser that may receive a refill bottle that supplies fragrance to the diffuser is provided. The diffuser includes a seat to facilitate easy placement and alignment of the refill bottle in the diffuser. The diffuser has an arm that can rotate about a pivot axis. The arm may rotate away from the seat to allow the user to place the refill bottle into the seat of the diffuser. The arm may also rotate towards the seat such that the arm can be placed over the refill bottle. The arm contains a piezo-electric component that can atomize the fragrance supplied by the refill bottle. The arm also includes a plurality of springs to create sufficient contact between the piezo and the refill bottle, to apply a downward force on the refill bottle, and to engage with a lock to secure the arm over the refill bottle.

3 Claims, 8 Drawing Sheets

FRAGRANCE DIFFUSER

CROSS-REFERENCE TO RELATED APPLICATIONS

This application claims priority to U.S. Provisional Patent Application Ser. No. 63/181,432, filed on Apr. 29, 2021, entitled "FRAGRANCE DIFFUSER," the entire disclosure of which is incorporated herein by reference.

FIELD OF INVENTION

The present invention relates generally to a fragrance diffuser, and more specifically to a smart fragrance diffuser having a piezo-electric component for use in homes, offices, and the like.

BACKGROUND OF THE INVENTION

Modern households generate a variety of odors that may be unpleasant to those living in the home, including odors emanating from trash cans, bathrooms, or pets living in the home. Thus, many consumers use products to neutralize unpleasant odors and/or fragrances with pleasing scents to mask unpleasant odors generated in the home.

For example, household sprays are disposed when a consumer sprays fragrance from a pressurized container while walking around the home. A heat source could also be used to disperse a fragrance (e.g., burning candle wicks, wax melts). These methods are inconvenient for the user because the fragrance must be manually released from its container, and heat sources must be activated. Further, these items present dangers to consumers, as high-pressure spray containers may explode if punctured, and many heat sources are a fire hazard.

Thus, manufacturers developed automatic fragrance dispensers that operate without user intervention and without using heat. These dispensers can be placed throughout the home to ensure that the fragrances contained within are evenly distributed throughout the home. Some of the automatic dispensers may even incorporate a timer or a "smart chip" to release fragrance at predetermined time intervals. Many of these "smart" dispensers accept refill bottles to reduce the diffuser's environmental impact and lower costs for consumers.

However, the automatic, "smart" diffusers present new issues for consumers. Many such smart diffusers accept refill bottles through a port in the bottom of the diffuser. Users must therefore insert a refill bottle into the device using an upward motion, causing the user to insert the refill bottle blindly, or hold the entire diffuser above the user's head. Inserting the refill bottle into the diffuser in this manner leads to two major problems.

First, when inserting the refill bottle blindly, a user cannot see if the refill bottle aligns with the receptor designed to accept the refill bottle, leading to frustration as the user may be required to make many attempts to align the refill bottle properly. Second, the user cannot see if the refill has been fully and properly inserted into the diffuser. If the refill bottle is not fully inserted into the diffuser, the diffuser may be disabled or unable to emit a full spray of fragrance. Also, if the user applies too much force when inserting the refill bottle and wedges the bottle into the diffuser, removal of the refill bottle can become quite difficult. Attempting to insert the bottle above the user's head is generally awkward and uncomfortable.

SUMMARY OF INVENTION

The present invention overcomes many of the shortcomings and limitations of the prior art devices discussed above. The invention is a fragrance diffuser system that generally includes a diffuser and a refill bottle. The diffuser may have a base and an arm that is rotatably connected to the base.

The base may generally include a top surface and a bottom surface. The bottom surface of the base may comprise rubber-like elements that may prevent the diffuser apparatus from sliding on a surface. A seat positioned and located on the base of the diffuser may be shaped such that a refill bottle can easily be received within the base of the diffuser. In addition, the seat may be shaped to receive the refill bottle in a desired orientation such that components of the refill bottle are in proper alignment to engage with the diffusion system. The seat preferably includes electrical contacts that can engage with a printed circuit board assembly ("PCBA") on the refill bottle to allow for communication between the refill bottle and the diffuser. The PCBA may communicate to the diffuser the type and/or amount of fragrance contained within the refill bottle so that the diffusion system may adapt its diffusion process to ensure a full spray of fragrance is released by the diffuser.

The arm of the diffuser can rotate about a pivot axis, either towards the base or away from the base. When the arm is rotated away from the base, a refill bottle may easily be placed into the seat of the base without the refill bottle contacting the arm. After the refill bottle is placed into the seat, the arm may be rotated towards the base until it engages with the refill bottle. The arm may include a channel that aligns with the refill bottle when the refill bottle is placed into the seat of the diffuser. Thereby, the user may simply apply a downward force to the arm to insert the top portion of the refill bottle into the channel of the arm. When the arm engages with the refill bottle, the fragrance contained within the refill bottle is ready to be diffused in the environment surrounding the diffuser.

The refill bottle includes a container having an internal cavity in which liquid fragrance can be contained. The refill bottle may also include a wick element that protrudes from the bottle, for example in an upward direction. The wick element may thereby draw liquid fragrance upwardly, for example via capillary action. The wick may be constructed to interface with the diffuser such that the liquid fragrance may be diffused by the diffuser. Further, since the position of the seat and the channel of the arm are predetermined, the wick is preferably properly aligned within the arm of the diffuser when the refill bottle is in the seat of the diffuser.

The PCBA on the bottom surface of the refill bottle may engage the electrical contacts in the seat of the diffuser when the refill bottle is placed in the diffuser. The bottom surface of the refill bottle may be shaped so that when it is placed into the seat of the diffuser, a proper connection is made between the PCBA and the electrical contacts without requiring the user to maneuver the refill bottle into the proper position. When the refill bottle is properly set into the seat of the base, the PCBA and the electrical contacts may form a portion of an electrical circuit. The electrical circuit is preferably completed when the arm of the diffuser is placed over the refill bottle. The completion of the electrical circuit allows electricity to flow through the diffuser so that it may operate.

The arm of the diffuser may contain a piezo-electric component (referred to hereinafter as a "piezo"). The piezo is configured to produce high-frequency sound waves when an electric current runs through it. The high-frequency sound waves may atomize liquids, such as the fragrance contained within the refill bottle, so that the liquid can diffuse throughout an environment. The piezo may be contained within a piezo housing that sits within the channel of the arm. When the arm is placed over a refill bottle, the piezo housing aligns with the wick of the refill bottle such that the wick is contained within the piezo housing. In this position, the wick may abut the piezo so that the high-frequency sound waves generated by the piezo can atomize the liquid fragrance on the wick, allowing the fragrance to diffuse throughout the environment. The length of time that the piezo operates may be predetermined so that a set volume of liquid is atomized each time the piezo is engaged, the set volume of liquid producing a "full spray" of the fragrance. Further, the amount of time that the piezo operates can be adjusted depending on the identity of the fragrance in the refill bottle, so that a full spray can be released no matter the type of liquid fragrance used with the diffuser.

The piezo housing may also include a piezo spring that sits within the housing above the piezo. The piezo spring applies a downward force on the piezo, ensuring that there is sufficient contact between the piezo and the wick to emit a full spray of fragrance from the diffuser. Further, the arm may include a second spring that sits above the piezo housing within the arm of the diffuser. The second spring may apply a downward force on the piezo housing, which in turn applies a downward force on the refill bottle. The downward force applied by the second spring may ensure that there is sufficient contact between the PCBA of the refill bottle and the electrical contacts in the seat of the diffuser so that the diffuser can operate.

The arm of the diffuser apparatus may be rotatably connected to the base of the diffuser by an axle. The axle, unless otherwise acted on, may apply a biasing force to the arm to rotate the arm away from the base of the diffuser apparatus. In one such case where the axle is acted upon, a lock in the body of the arm and a hinge may be used to maintain the arm in position when it is placed over a refill bottle. The hinge may be immobile relative to the axle. When the lock is positioned under the hinge, the arm may no longer rotate away from the base of the diffuser apparatus.

When the user wishes to restore bias to the arm, the user may push an unlock button. The unlock button may apply a force to the lock, which may push the lock out from under the hinge. When this occurs, the axle may again lift the arm away from the base of the diffuser apparatus.

The diffuser embodiments described improves upon diffusers available on the market. First, the refill bottle may be received by a seat in the base of the diffuser that the user can easily see when using the diffuser. The seat may also align the refill bottle so that the refill bottle may properly interact with the diffusion system within the diffuser. Second, the diffuser has an arm that the user places over the top of the refill bottle. The user may place the arm over the refill bottle by applying a downward force to the arm. Thus, the user can easily ensure that the refill bottle is fully engaged with the diffusion system so that a full spray of fragrance may be released from the diffuser each time the diffuser is activated. Finally, the refill bottle may easily be removed from the diffuser; the user simply needs to lift the arm upwardly and away from the refill bottle and take the refill bottle out of the seat of the diffuser.

These and other aspects and advantages of the present invention will become apparent to those skilled in the art after considering the following detailed description in connection with the accompanying drawings.

Figure 1:
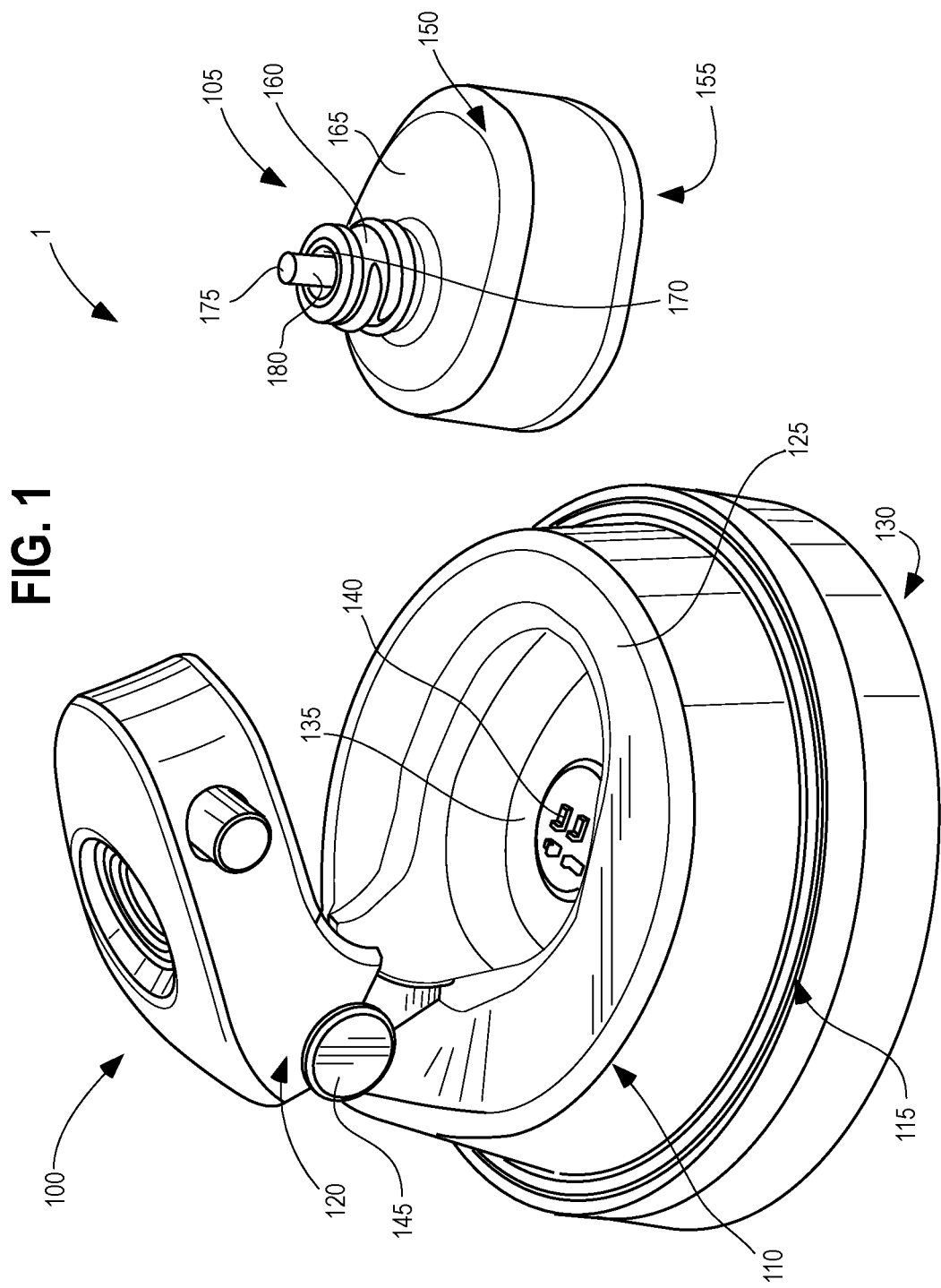
FIG. 1 is an isometric view of a diffuser system including a diffuser and a refill bottle.

While the disclosure is susceptible to various modifications and alternative forms, a specific embodiment thereof is shown by way of example in the drawings and will herein be described in detail. It should be understood, however, that the drawings and detailed description presented herein are not intended to limit the disclosure to the particular embodiment disclosed, but to the contrary, the intention is to cover all modifications, equivalents, and alternatives falling within the spirit and scope of the present disclosure as defined by the appended claims.

DETAILED DESCRIPTION

The invention will now be described with reference to the drawing figures, in which like reference numerals refer to like parts throughout. For purposes of clarity in illustrating the characteristics of the present invention, proportional relationships of the elements have not necessarily been maintained in the drawing figures.

FIG. 1 illustrates a first embodiment of a fragrance diffuser system 1 for diffusing fragrance. Generally, the system 1 may include a diffuser 100 and a fragrance bottle or a refill bottle 105. The diffuser 100 may be configured to diffuse fragrance supplied by the refill bottle 105. As described in additional detail below, the diffuser 100 is configured to allow a user to easily insert the refill bottle 105 into the diffuser 100 by placing the refill bottle 105 within the diffuser 100. In addition, the diffuser 100 can be adapted such that a "full spray" of fragrance can be released by the diffuser 100 regardless of the type of fragrance contained within the refill bottle 105.

The diffuser 100 may have a body 110 that includes a base 115 and an arm 120. The base 115 may be provided in the form of a cylinder (though other shapes are foreseeable) with a top surface 125 and a bottom surface 130. The top surface 125 may include a concave seat 135 that is formed as an indentation in the top surface 125 of the base 115. The seat 135 may be shaped to receive the refill bottle 105. Further, the seat 135 may have electrical contacts 140 that allow electric components (not illustrated) of the diffuser 100 to interface with the refill bottle 105.

The arm 120 is shown in a first "open" position. The arm 120 is rotatably connected to the base 115 at a pivot axis 145. The arm 120 may rotate about the pivot axis 145 in a first "open" direction away from the base 115 and in a second "closed" direction towards the base 115. When the arm 120 has fully rotated in the open direction to the open position, the user may place the refill bottle 105 into the seat 135.

The refill bottle may have a body 150 with a bottom portion 155 that may be shaped to sit in and be received by the seat 135. Sitting the refill bottle 105 in the seat 135 may help prevent the refill bottle 105 from tipping over when it sits in the diffuser 100. Sitting the refill bottle 105 in the seat 135 may also help provide a proper alignment between the electrical contacts 140 and the refill bottle 105.

A neck member 160 may extend above a top portion 165 of the refill bottle 105. The neck member 160 includes an aperture 170 that extends through the neck member 160 and into the body 150 of the refill bottle 105. The neck member 160 may provide a pathway through which the fragrance stored in the refill bottle 105 can be delivered to the diffuser 100 via a wick 175.

The wick 175 is preferably disposed in the aperture 170. The wick 175 may be an enclosed cylinder (though other shapes are foreseeable) with an upper portion 180. The diameter of the wick 175 may be substantially the same as, or just smaller than, the diameter of the aperture 170 so that the wick 175 is retained within the aperture 170 by a friction fit. The wick 175 extends upwardly from the body 150 of the refill bottle 105, through the aperture 170, and above the neck member 160. The wick 175 facilitates the transfer of the fragrance through the neck member 160 through a physical process such as capillary action, or another similar physical phenomenon, as would be appreciated by those in the art. The capillary action draws the fragrance through the wick 175 to the upper portion 180 so that the fragrance may be dispersed by the diffuser 100.

Figure 2:
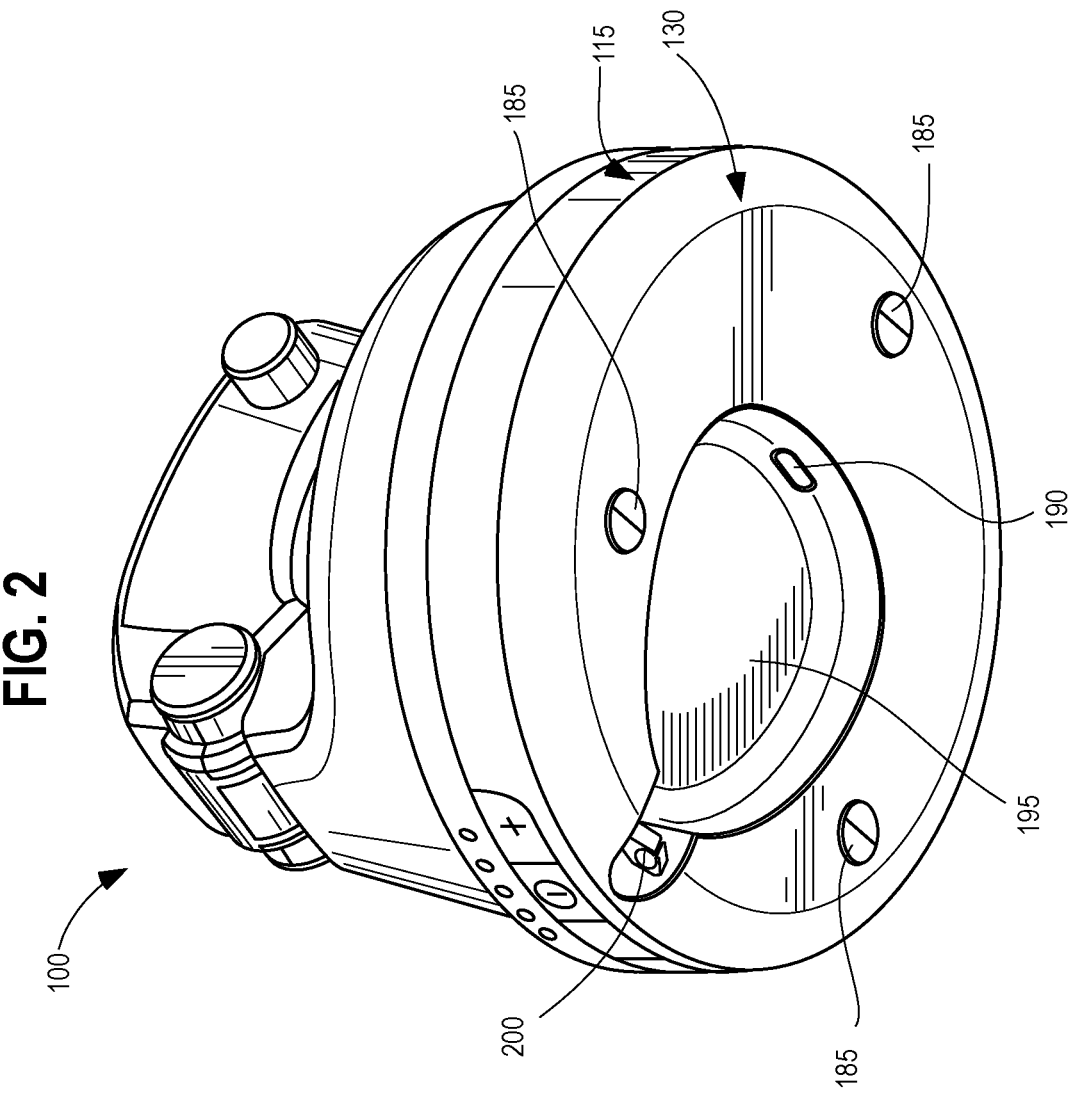
FIG. 2 is a bottom isometric view of the diffuser of FIG. 1.

As illustrated in FIG. 2, the bottom surface 130 of the diffuser 100 may have footings 185. The footings 185 may be formed in the shape of a circular pad and affixed to the bottom surface 130. The footings 185 may have a low profile such that they may not impact the overall stability of the base 115. Also, the footings 185 may be composed of rubber or another high-friction material to prevent the diffuser from sliding upon a surface it is disposed on. In an alternative embodiment, the bottom surface 130 may be equipped with a high-friction coating rather than footings to prevent the diffuser 100 from sliding.

The bottom surface 130 may also include a port 190 that may be positioned within a cavity 195 of the bottom surface 130. The port 190 may be shaped to receive an electrical cord (not illustrated) or another equivalent power source that can supply an electrical current to operate the diffuser 100. To help prevent the electrical cord from being accidently removed from the port 190, a cord guide 200 may be provided. The cord guide 200 is affixed to the bottom surface 130 and disposed of in the cavity 195. As shown in FIG. 2, the cord guide 200 is provided in the form of a pinched u-shape to allow for the cord to be retained in the cord guide 200 and to also allow for removal and placement of a cord in the cord guide 200, though other structures are envisioned. Finally, the cavity 195 may prevent the base 115 from resting on the electrical cord, which would decrease the stability of the diffuser 100.

In alternative embodiments, the diffuser 100 may be equipped with an internal power source, such as a battery. The battery may be disposed of in the cavity 195 or within the body 110 of the diffuser 100.

Figure 3:
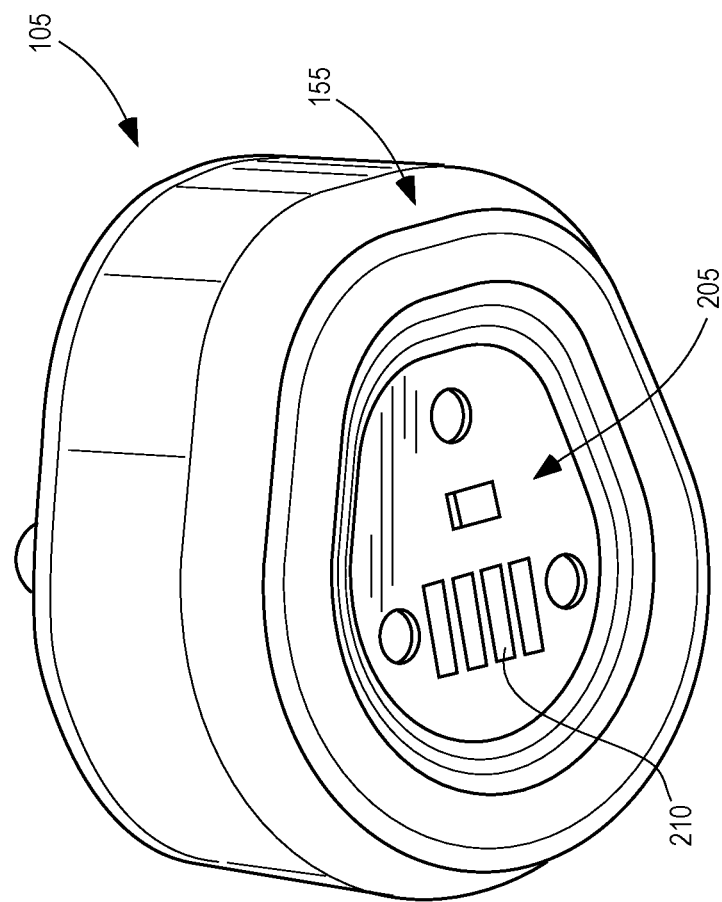
FIG. 3 is a bottom isometric view of the refill bottle of FIG. 1.

Turning to FIG. 3, the bottom portion 155 of the refill bottle 105 may include a printed circuit board assembly ("PCBA") 205. The PCBA 205 is preferably composed of a non-conductive surface upon which electrical components may be affixed and connected to one another. The PCBA 205 may have contacts 210 that may engage with the electrical contacts 140 on the base 115. In addition, the circuitry of the PCBA 205 (not illustrated) may, for example, store information regarding the type of fragrance contained in the refill bottle 105 and/or measure and store the amount of fragrance remaining in the refill bottle 105. The PCBA 205, when connected to the diffuser 100, may communicate the information stored within the circuitry of the PCBA 205 to the diffuser 100. Based on the communicated information, the diffuser 100 may adjust its diffusion process to account for the different physical properties of different types of fragrances, so that a full spray of fragrance may be released by the diffuser 100.

Figure 4:
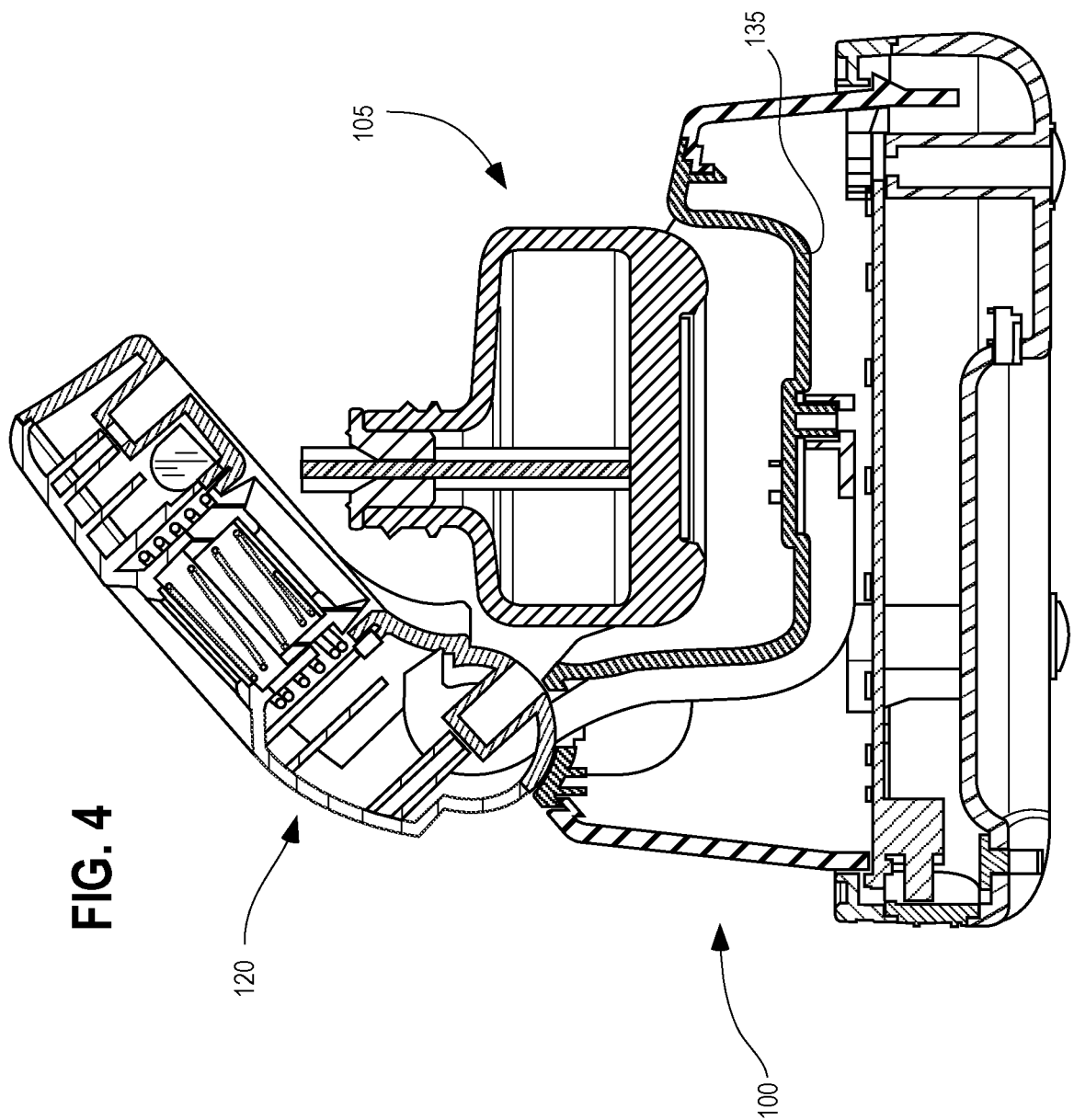
FIG. 4 is a side elevation cross-sectional view of the diffuser and the refill bottle, the refill bottle disposed in a seat of the diffuser and an arm of the diffuser in a first, open position.

FIG. 4 illustrates a sectional view of the diffuser 100 and the refill bottle 105 when the arm 120 is in the open position. When the arm 120 is in the open position, the user may place the refill bottle 105 into the seat 135 of the diffuser 100.

Figure 5:
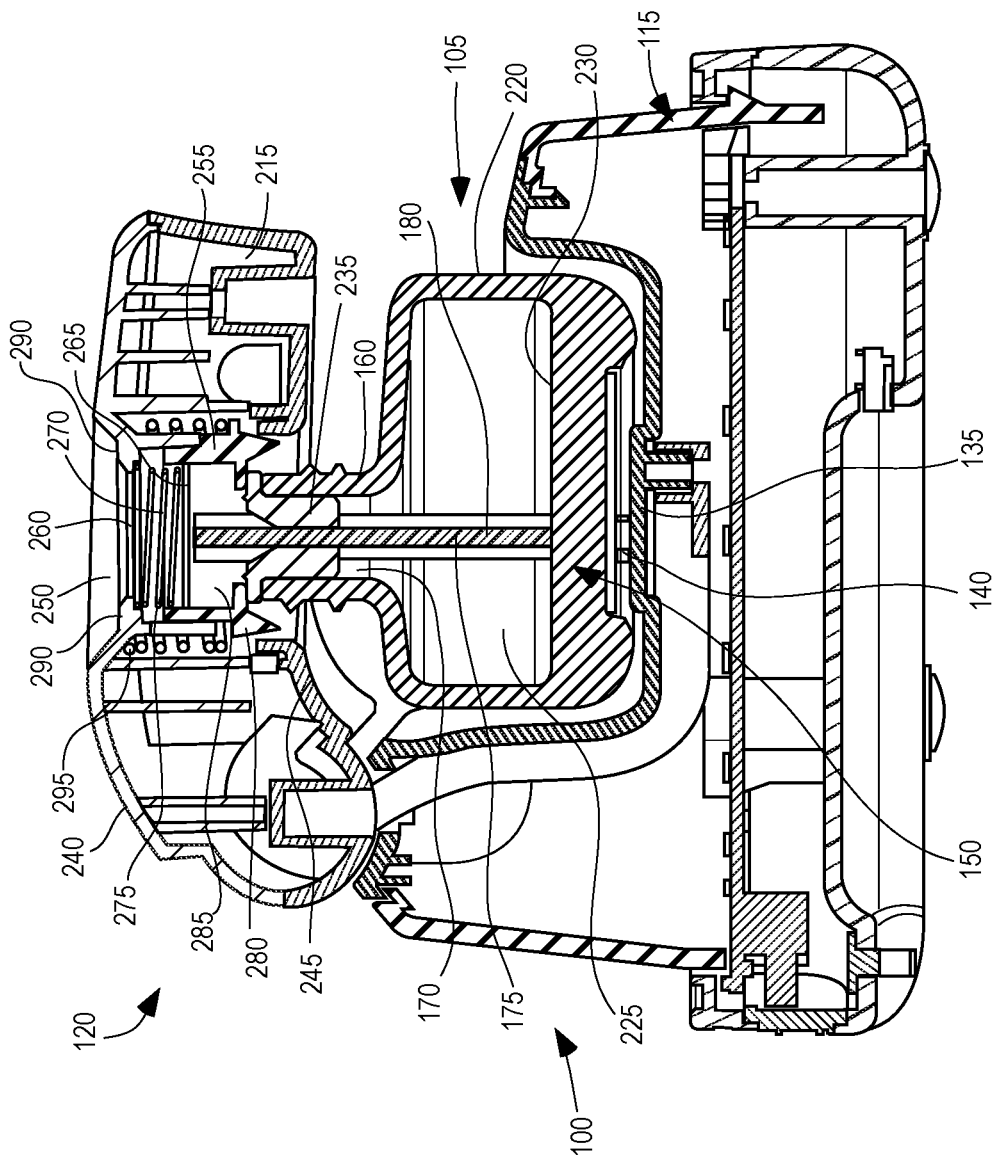
FIG. 5 is a side elevation cross-sectional view of a refill bottle disposed in the seat of the diffuser and the arm of the diffuser in a second, closed position.

FIG. 5 illustrates a sectional view of the diffuser 100 and the refill bottle 105 as the refill bottle 105 sits in the seat 135. The arm 120 of the diffuser 100 is in a second, or "closed" position, placing the arm 120 over the top of the refill bottle 105 and substantially parallel with the base 115 of the diffuser 100. When the arm 120 is in the closed position and the refill bottle 105 is positioned within the seat 135, the neck member 160 and the wick 175 of the refill bottle 105 preferably extend into a body 215 of the arm 120.

The body 150 of the refill bottle 105 includes an interior surface 220 that defines an interior cavity 225. The interior cavity 225 may contain the fragrance that is supplied to the wick 175. The wick 175 may extend from a bottom surface 230 of the interior cavity 225, through the aperture 170, and extend upwardly beyond the neck member 160. The wick 175 may extend to the bottom surface 230 so that fragrance contained within the interior cavity 225 may be drawn into the arm 120 via the wick 175.

The neck member 160 may also include a seal member 235 that circumscribes the wick 175. The seal member 235 is preferably made of an elastic or elastic-like material to seal any space formed between the wick 175 and the neck member 160. The seal member 235 may retain the wick 175 in an upright position and keep it stationary such that it can effectively engage with the diffusor 100. The seal member 235 may also effectively decrease the diameter of the aperture 170 so that the fragrance does not evaporate from the refill bottle 105 as quickly. The seal member 235 may also help prevent the fragrance from leaking from the refill bottle 105 if the refill bottle 105 is tipped on its side.

The arm 120 includes a top surface 240 and a bottom surface 245. The arm 120 preferably includes a channel member 250 that extends throughout the body 215, extending from the top surface 240 to the bottom surface 245. The diameter of the channel member 250 may be substantially the same throughout its length, or the channel member 250 may be tapered at either of its ends. When the refill bottle 105 is in the seat 135 and the arm 120 is in the closed position, the neck member 160 and the wick 175 may extend into the channel member 250.

A piezo housing 255 may be retained within and affixed to an interior surface 260 of the channel member 250. The piezo housing 255 contains a piezo 265 and a piezo spring 270. The piezo spring 270 may be positioned and located above the piezo 265 in the piezo housing 255 and applies a predetermined downward force to the piezo 265. A top portion 275 and a bottom portion 280 of the piezo housing 255 may define a void 285 in the piezo housing 255. In the illustrated embodiment, the diameter of the void 285 at the bottom portion 280 is smaller than its opening at the top portion 275; however, in other embodiments the size and shape of the void 285 may vary, as would be appreciated by one skilled in the art.

Lip elements 290 may protrude inwardly from the top surface 240 of the arm 120 and downwardly into the channel member 250. The lip elements 290 may restrict the diameter of the channel member 250 such that the piezo spring 270 may be retained within the channel member 250. The piezo spring 270 may be sized to have a larger diameter than both the opening of the void 285 at the bottom portion 280 and the diameter of the channel member 250 where the piezo spring 270 abuts the lip elements 290.

The piezo 265 may be composed of a crystalline material, such as quartz, that is mechanically deformed when an electric current is applied to the piezo 265. Materials suitable to use as a piezo are well known in the art. The piezo 265 may be connected to a circuit board (not illustrated) that controls the timing and amount of electric current sent to the piezo 265. The piezo 265 may vibrate at different rates depending upon the amount of electric current running through it. At predetermined levels of electric current, the piezo 265 may vibrate such that it emits high-frequency sound waves capable of atomizing liquids. The atomized liquid may then diffuse into the air and away from the piezo 265, and thus away from the diffuser 100 via the wick 175.

Different fragrances used with the diffuser 100 may have different physical properties. As such, the frequency emitted by the piezo 265 may be altered to match the optimal sound-wave frequencies required to efficiently diffuse each fragrance (as determined by laboratory tests). As a non-limiting example, the piezo 265 may be configured to emit a first frequency for a first fragrance and a second frequency for a second fragrance. Thus, altering the frequency emitted from the piezo 265 helps provide that a full spray of the fragrance is emitted from the diffuser 100, no matter the identity of the fragrance used.

When the refill bottle 105 sits in the seat 135 and the arm 120 is in the closed position, at least a portion of the wick 175 may extend into the piezo housing 255. More specifically, the wick 175 of the refill bottle 105 may extend into the void 285 and abut the piezo 265. The piezo spring 270 helps to provide sufficient contact between the wick 175 and the piezo 265 such that the high-frequency sound waves emitted by the piezo 265 vaporize the fragrance transferred to the upper portion 180 of the wick 175.

An arm spring 295 may be contained within the channel member 250 between the piezo housing 255 and the lip elements 290. The arm spring 295 may substantially surround the piezo housing 255. When the arm 120 is in the closed position, the arm spring 295 applies a predetermined downward force on the piezo housing 255. In turn, the piezo housing 255 applies a downward force on the refill bottle 105. The amount of force supplied by the arm spring 295 is sufficient to establish a connection between the PCBA 205 of the refill bottle 105 and the electrical contacts 140 in the seat 135. Thus, when the arm 120 is in the closed position, an electrical circuit within the diffuser 100 is completed to such that an electric current may flow through the diffuser 100.

In the preferred embodiment, the force applied by the piezo spring 270 to the piezo 265 is less than the amount of force applied by the arm spring 295 to the piezo housing 255. However, in other embodiments, the amount of force applied by the piezo spring 270 and the arm spring 295 may be the same, or the amount of force applied by the piezo spring 270 may be greater than the force applied by the arm spring 295. Further, in yet other embodiments, the piezo spring 270 and the arm spring 295 may be replaced by a single spring or a single spring system that could apply a downward force to both the piezo 265 and the piezo housing 255.

Figure 6:
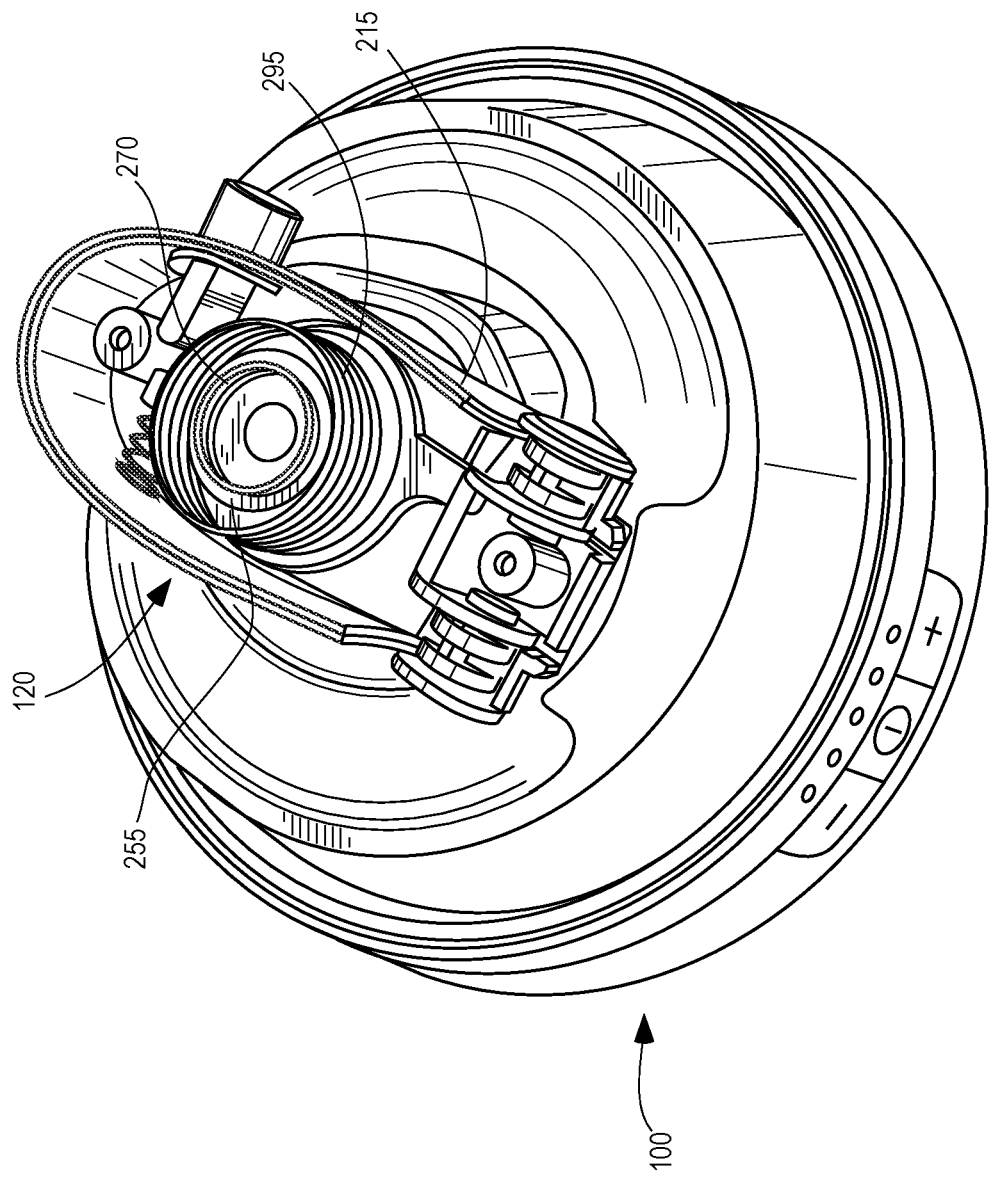
FIG. 6 is a top isometric view of the diffuser and refill bottle of FIG. 5, with a top portion of the arm of the diffuser removed.
Figure 7:
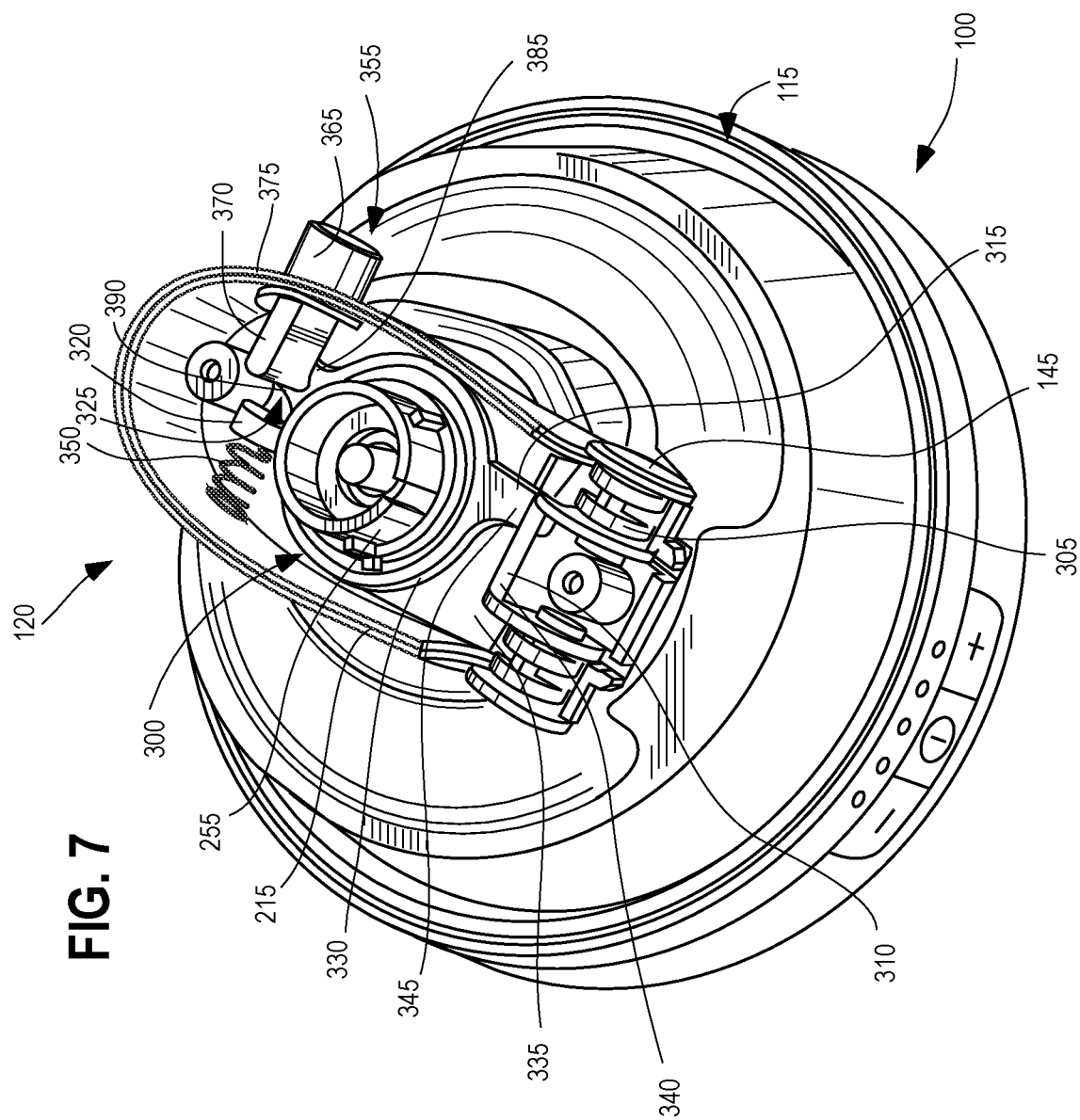
FIG. 7 is a top isometric view of the diffuser and refill bottle of FIG. 5, with a top portion of the arm of the diffuser removed.
Figure 8:
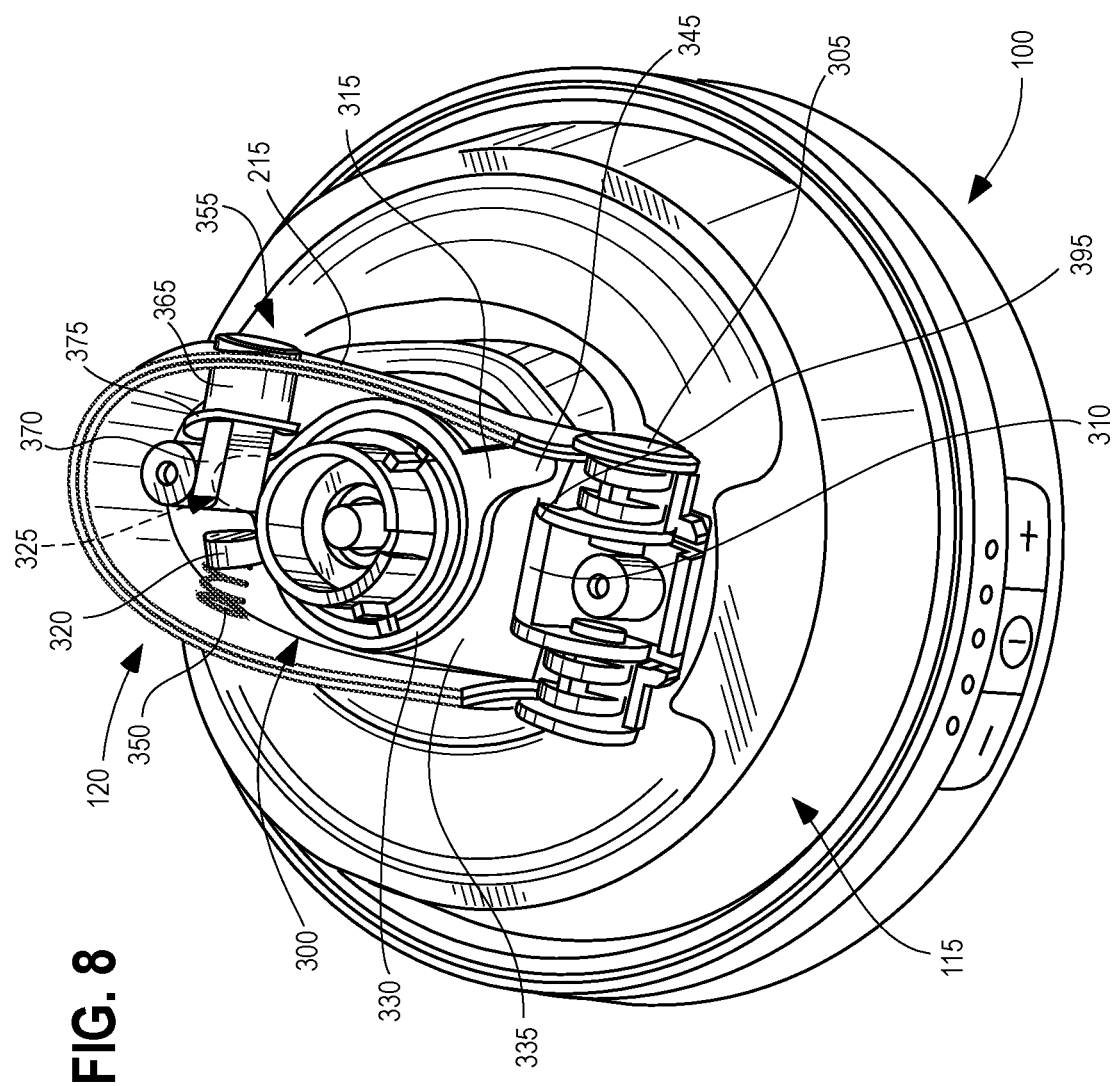
FIG. 8 is a top isometric view of the diffuser and refill bottle of FIG. 5, with a top portion of the arm of the diffuser removed and an unlock button on the arm pressed.

FIGS. 6-8 illustrate the arm 120 in the closed position; in these figures the top portion of the arm 120 is removed so that the interior of the diffuser is more clearly illustrated. FIG. 6 illustrates an embodiment of the diffuser 100 in which the piezo spring 270 is contained within the piezo housing 255 and the arm spring 295 surrounds the piezo housing 255. In other embodiments, the arm spring 295 and the piezo spring 270 may be located elsewhere within the arm 120, as would be appreciated by those skilled in the art.

In FIGS. 6 and 7, the arm 120 is secured in the closed position by a lock 300 in a first position, while in FIG. 8 the lock 300 is disengaged by being placed into a second position. While FIGS. 6 and 7 illustrate an embodiment of the lock 300 that can secure the arm 120 in the closed position, other embodiments of the lock 300 may also secure the arm 120 in the open position.

Turning to FIG. 7, the arm 120 is preferably rotatably connected to the base 115 of the diffuser 100 at the pivot axis 145. The rotation of the arm 120 may be effectuated by an axle 305 affixed to the base 115 at the pivot axis 145. The axle 305 may cause the arm 120 to rotate in the open direction (away from the base 115 of the diffuser 100) and in the closed direction (towards the base 115). In some embodiments, the axle 305 may be biased to rotate in the open direction until the arm 120 reaches the open position. To counteract this bias, a user may supply a force to the arm 120 to rotate the arm 120 in the closed direction until it reaches the closed position. In other embodiments, the axle 305 may be biased to rotate the arm 120 in the closed direction, or the axle 305 may be biased to rotate the arm 120 in both the open direction and the closed direction. Other equivalent systems that may effectuate the rotation of the arm 120 would be appreciated by those skilled in the art.

The lock 300 may secure the arm 120 in the closed position by engaging with a hinge element 310 of the axle 305. In the embodiment illustrated in FIG. 7, the lock 300 is composed of a first arm 315, a second arm 320, a third arm 325, and a rotation body 330, though other structures are envisioned. The arms 315, 320, 325 may be formed in one piece with the rotation body 330. The first arm 315 and the second arm 320 may be located on opposite ends of the rotation body 330, and the third arm 325 may be adjacent to the second arm 320. The rotation body 330 may be formed in the shape of a disk and rotatably connected to an interior surface 335 of the arm 120 such that the rotation body 330 surrounds the piezo housing 255. In other embodiments, the lock 300 may be disposed elsewhere within the body 215 of the arm 120.

The hinge element 310 may be u-shaped, though other shapes are foreseeable, and includes a top surface 340 and a bottom surface (not illustrated). The hinge element 310 may protrude from the axle 305 and into the body 215 of the arm 120. Also, the hinge element 310 may be immobile relative to the axle 305. When the lock 300 is in the first position, a top surface 345 of the first arm 315 abuts the bottom surface of the hinge element 310. The placement of the first arm 315 under the hinge element 310 may prevent the arm 120 from rotating away from the base 115 of the diffuser 100.

A spring 350 may rotate the lock 300 into the first position. The spring 350 may be affixed to the interior surface 335 of the arm 120 adjacent to the second arm 320. The spring 350 may apply a force to the second arm 320, rotating the lock 300 in a clockwise direction. As the lock 300 rotates towards the first position, the first arm 315 is forced under the hinge element 310. The clockwise rotation of the lock 300 may continue until further rotation in the clockwise direction is prevented by an unlock button 355.

The unlock button 355 extends into the body 215 of the arm 120 through an aperture (not illustrated) in the arm 120. In the embodiment illustrated in FIG. 7, the unlock button 355 generally comprises a cylinder 365, a protrusion 370, and a lip element 375, though other structures are envisioned. The cylinder 365 and the protrusion 370 may be on opposite ends of the unlock button 355 and separated by the lip element 375. The cylinder 365 may extend through the aperture and into the body 215 of the arm 120 and may be sized to have substantially the same diameter as the aperture.

The protrusion 370 and the lip element 375 may be positioned within the body 215 of the arm 120. The third arm 325 may include a first stem 385 and a second stem 390 adapted to receive the protrusion 370 such that the protrusion 370 may interact with the lock 300. More specifically, the first stem 385 may be shorter than a second stem 390 such that the protrusion 370 may abut the second stem 390 when the protrusion 370 is received in the third arm 325.

The lip element 375 may be sized to have a wider diameter than the aperture in the arm 120 to prevent the unlock button 355 from being expelled from the body 215 when the lock 300 rotates in the clockwise direction. When the lip element 375 abuts the interior surface 335 of the arm 120, further clockwise rotation of the lock 300 is prevented.

When the refill bottle 105 is empty, the user may wish to remove the refill bottle 105 from the diffuser 100. To remove the refill bottle 105, the user may disengage the lock 300 so that the arm 120 may return to the open position.

As illustrated in FIG. 8, the lock 300 may be disengaged by being placed in the second position. When the lock 300 is in the second position, the bottom surface of the hinge element 310 no longer abuts the top surface 345 of the first arm 315. When the lock is in the second position, the axle 305 may rotate the arm 120 away from the base 115 of the diffuser 100, as described in greater detail below.

To disengage the lock 300, the user may press the unlock button 355. When the unlock button 355 is pressed, the protrusion 370 applies a force to the third arm 325, which in turn causes the rotation body 330 to rotate in the counterclockwise direction. As the rotation body 330 rotates in the counterclockwise direction, the spring 350 is compressed by the second arm 320 and the cylinder 365 slides into the body 215 of the arm 120. As the counterclockwise rotation of the rotation body 330 continues, the first arm 315 rotates away from the hinge element 310 until it no longer abuts the hinge element 310. Then, the axle 305 may lift the arm 120 away from the base 115 of the diffuser 100 until the interior surface 335 abuts the bottom surface of the hinge element 310. When the interior surface 335 abuts the hinge element 310, the arm 120 is in the open position. After the arm 120 reaches the open position, and the unlock button 355 is no longer pressed, the hinge element 310 may prevent the clockwise rotation of the lock 300 because a side portion 395 of the hinge element 310 may abut the first arm 315. By preventing the clockwise rotation of the lock 300, the side portion 395 may prevent the lock 300 from returning to the first position. If the user wishes to re-engage the lock 300, the arm may be returned to the closed position. As the user lowers the arm 120 towards the base 115 of the diffuser 100, an opening (not illustrated) may form between the hinge element 310 and the interior surface 335. Once the opening reaches a predetermined size, the first arm 315 may translate below the hinge 310, and the lock 300 may return to the first position as illustrated in FIG. 7.

As is evident from the foregoing description, certain aspects of the present invention is not limited by the particular details of the examples illustrated herein, and it is therefore contemplated that other modifications, applications, variations, or equivalents thereof, will occur to those skilled in the art. Many such changes, modifications, variations and other uses and applications of the present constructions will, however, become apparent to those skilled in the art after considering the specification and the accompanying drawings. In addition, unless mention was made above to the contrary, it should be noted that all of the accompanying drawings are not to scale. All such changes, modifications, variations and other uses in applications which do not depart from the spirit and scope of the present inventions are deemed to be covered by the inventions which are limited only by the claims which follow.

What is claimed is:

1. A diffuser for activating a fragrance bottle, the diffuser including:
   a body;
   an arm rotatably coupled to the body;
   wherein when the arm is in a first position, the arm abuts at least a portion of the fragrance bottle and the diffuser is activated;
   wherein when the arm is in a second position, the arm and the fragrance bottle do not abut each other;
   the arm further including a piezo housing, the piezo housing configured to retain a piezo, the piezo being positioned and located below a piezo spring; and
   wherein when the arm is in the first position:
   a portion of a wick of the fragrance bottle is received in the piezo housing;
   the wick abuts the piezo; and
   the piezo spring exerts a downwardly directed force on the piezo that is less than a downwardly directed force exerted by an arm spring on the fragrance bottle.

2. The diffuser of claim 1, wherein in the first position the arm is generally parallel with the body, and wherein in the second position the arm extends away from the body.

3. The diffuser of claim 1, the arm further including:
   an axle;
   a lock comprising:
     a rotatable body; and
     a spring positioned and located adjacent to the rotatable body such that the spring applies a force to the rotatable body;
   an unlock button extending into the arm, the unlock button abutting the rotatable body; and
   wherein the axle prevents the motion of the arm of the diffuser away from the first position when the unlock button is in a locked position.

* * * * *